United States Patent [19]

Braun et al.

[11] Patent Number: 4,671,794
[45] Date of Patent: Jun. 9, 1987

[54] LARYNGEAL INJECTOR

[75] Inventors: William G. Braun, Los Altos; Philip R. Palin, Sunnyvale; Brent L. Von Moll, Mountain View; Tony F. L. Lai, Mountain View, all of Calif.

[73] Assignee: Collagen Corporation, Palo Alto, Calif.

[21] Appl. No.: 788,928

[22] Filed: Oct. 18, 1985

[51] Int. Cl.⁴ .............................................. A61M 5/325
[52] U.S. Cl. .................................................... 604/240
[58] Field of Search ............................ 604/240–243, 604/158–167, 198, 224, 272, 232

[56] References Cited

U.S. PATENT DOCUMENTS

| | | | |
|---|---|---|---|
| 2,740,404 | 4/1956 | Kohl | 604/198 X |
| 2,748,767 | 6/1956 | Wright | 604/232 X |
| 2,923,295 | 2/1960 | Guerriero | 604/164 |
| 3,870,043 | 3/1975 | Dunn | 604/272 |
| 4,364,388 | 12/1982 | Cech | 604/224 |

Primary Examiner—John D. Yasko
Attorney, Agent, or Firm—Ciotti & Murashige

[57] ABSTRACT

An injector is disclosed for administering fluids such as medications and tissue-augmenting suspensions of collagen to laryngeal tissues. The injector includes a needle, a hollow connector tube, and a syringe receiver into which syringes of collagen or a like low-viscosity fluid are inserted. The injector is adapted for one-hand operation and the serial use of several syringes of collagen or like fluid.

5 Claims, 4 Drawing Figures

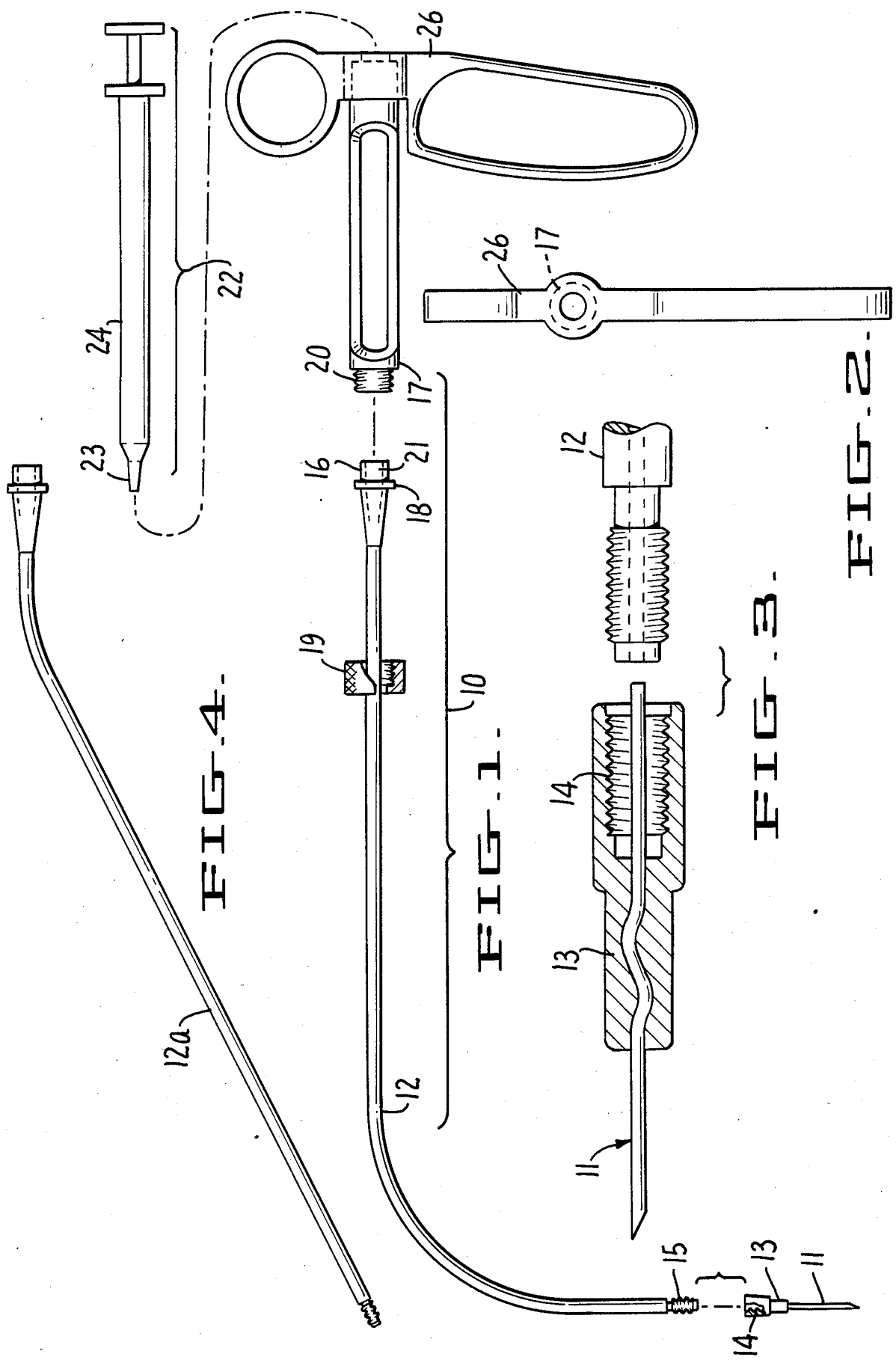

LARYNGEAL INJECTOR

FIELD OF THE INVENTION

This invention is in the field of medical devices. This invention relates to devices for injecting solutions and dispersions into inaccessible tissues. In a preferred embodiment, it concerns a device especially adapted for injecting solutions and dispersions into tissues of the larynx.

BACKGROUND OF THE INVENTION

Human vocal cords and other soft tissues of the larynx occasionally require medication or augmentation. Medication often takes the form of anesthesia. Augmentation can, for example, be required to replace diseased tissue that has been removed surgically, or it can be required to correct a naturally occurring inadequate seal between the vocal cords. Preferably, the augmentation is carried out nonsurgically by injecting a suitable paste or fluid substance into the tissue requiring augmentation. A paste of poly(tetrafluoroethylene) (Teflon ®) has been used for the purpose in the past (see, for example, Ward, "Uses of Injectable Teflon in Otolaryngology", *Arch Otolaryng*, vol. 87, June 1968, pp. 91–97).

Recently, Collagen Corporation has suggested that essentially nonantigenic exogenous collagen could be used for treating this indication. An essentially nonantigenic bovine collagen for augmenting soft tissue defects has ben marketed by Collagen Corporation under the trademark ZYDERM ®. An injectable glutaraldehyde cross-linked form of this collagen has been developed for the same use and is described in published European Patent Application No. 83301135.6 (published on Sept. 21, 1983).

In such an application, collagen offers a number of advantages. For one, it is very persistent—that is, it is not prone to migration or dispersal after injection. It is very biocompatible and has the potential for administration with greater accuracy and precision because it is relatively low in viscosity as compared with the Teflon pastes. Proteoglycan and other low viscosity natural or synthetic biopolymers can be used as well.

In order to realize these advantages, however, special injection devices are required to enable the collagen suspension to be properly and precisely delivered to the relatively inaccessible tissues of the larynx. It is an object of this invention to provide such an injection device.

STATEMENT OF THE INVENTION

In accord with this invention, an injector for administering medication or augmentation to tissues of the larynx is provided. In a preferred application the injector is for administering collagen augmentation to such tissues. The injector includes a fine-gauge hypodermic needle, a rigid double open-ended hollow connector tube, and a syringe receiver carrying an external handle assembly. The needle is threadably attached to and in communication with one end of the connector tube. The other open end of the connector tube is attached to the syringe receiver assembly. This end of the tube is adapted to engage, with a liquid-tight seal, a syringe tip such that the syringe contents can pass through the connector tube to the hypodermic needle. The receiver is adapted to receive and support the syringe body and position the syringe plunger immediately adjacent to the external handle such that with one hand the needle can be placed in the laryngeal tissue and the syringe plunger activated to inject the fluid into the tissue. As injectable collagen is generally commercially available packed in single-use disposable syringes, the receiver and the syringe attaching end of the connector tube preferably are adapted to receive and attach to a disposable syringe.

DETAILED DESCRIPTION OF THE INVENTION

Brief Description of the Drawings

The invention will be further described with reference to the drawings which accompany this specification and claims. In the drawings:

FIG. 1 is an exploded partially cut-away side view of a laryngeal injector of the invention;

FIG. 2 is a rear view of the handle and syringe receiver of the injector;

FIG. 3 is an expanded-scale cut-away detail of the screw-on needle assembly used in the laryngeal injector; and FIG. 4 is a side view of an alternate connector tube for use in the laryngeal injector.

DESCRIPTION OF THE PREFERRED EMBODIMENT

In FIG. 1, an injector 10 of this invention is shown. Injector 10 includes a hypodermic needle 11 attachable to connector tube 12. Needle 11 is a very fine-gauge needle such as 24 gauge or finer, preferably 27 gauge or finer. This fine gauge is advantageous for precise placement of the medication or augmentation. This advantage is especially beneficial during the administration of collagen augmentation dispersions and the like. Its use is possible with collagen because the collagen suspension is suitably fluid and nonviscous to permit its passage through such a needle without undue pressure, plugging, or like problems. Needle 11 is usually a single-use disposable needle, although if desired, a multi-use needle could be employed. The hub 13 of needle 11 is as narrow as possible to minimize visual blockage when the physician is placing the needle in the laryngeal tissues. Hub 13 carries internal threads 14 which threadably engage corresponding threads 15 on the distal end of hollow connector tube 12. Connector tube 12 has the following characteristics: it is rigid, about 1.0 to about 2.5 mm in outside diameter, and about 200–300 mm in length. The outside diameter of tube 12 is generally selected as small a practically possible, again to minimize visual interference while the physician is placing the needle in the laryngeal tissues. The length is a length effective to reach from the patient's mouth to the laryngeal tissues.

The inside diameter of the connector tube is, of course, related to the outside diameter and can range from about 0.5 to about 1.5 mm. It is preferred to have a small inside diameter, as this minimizes dead volume, which can be a significant issue because injectable collagen is a relatively valuable material. The proximal end of open-ended connector tube 12 flares into a connector hub 16 which is sized to engage and fit into the end of syringe receiver 17. A stop collar 18 adjacent to hub 16 limits the travel of hub 16 into receiver 17. Knurled ferrule 19 is pulled up over the flared proximal end of tube 12 and engages threads 20 on receiver 17 to affix tube 12 to receiver 17.

The inside of the flared end of tube 12 is sized to be a liquid-tight friction fit with the tapered tip 23 of syringe 22. Syringe 22 includes barrel 24 and plunger 25. The inside diameter of receiver 17 is sized to correspond to the outside diameter of barrel 24 so that syringe 22 can be inserted into receiver 17 and receiver 17 can support and align syringe 22 into liquid-tight engagement with connector tube 12. (This feature is more clearly shown in FIG. 2, which is an end view looking into receiver 17.)

This configuration of receiver 17 is especially advantageous for use with injectable collagen as it is available commercially in prefilled disposable syringes. This configuration allows a plurality of prefilled sterile syringes to be inserted serially into receiver 17 once needle 11 is placed in the laryingeal tissue without the necessity of removing and replacing the needle in the tissue. This speeds the procedure and minimizes patient discomfort.

Receiver 17 is attached to handle 26. Handle 26 is shaped and positioned to permit engagement of the handle by the physician's fingers and actuation of plunger 25 by the physician's thumb. This one-handed operation is an important advantage of the invention as it frees the other hand to direct light or to clear the physician's view to the inaccessible laryngeal tissues being augmented.

Another advantage of this injector is that the physician has total control of the extrusion of material. Since an extrusion device with a mechanical advantage or mechanical drive is not required to extrude low viscosity materials such as collagen suspensions or dispersions, the physician has a better feel for the injection technique. Also, unlike mechanical injection devices which may have significant run-on problems after the removal of the driving force, the extrusion of material with the device of this invention stops as soon as the physician stops applying force to the syringe plunger.

Turning to FIG. 3, briefly, this figure depicts, in expanded scale, the screw-on attachment of needle 11 to connector tube 12. It also shows a preferred needle construction in which the cannula of the needle extends back through threads 14 so as to enter the inside of tube 12. This strengthens the coupling and guards against accidental breakage and needle loss. So to, the threaded coupling of needle 11 to tube 12 gives a firm positive attachment with minimal hazard of needle loss in use in the inaccessible and critical larynx region.

Tube 12 is depicted as angled by about 90°. This is not critical. As shown by FIG. 4, other shapes for tube 12, such as tube 12a, are possible and are chosen based on the shape of the patient's airway and the physician's preference.

All components of the injector of this invention are either disposable or made of materials which can be sterilized. Usually, the only parts disposed of are the needle and the syringe body itself. The handle, the connector tube and the carrier are typically fabricated from 304 stainless steel or a similar sterilizable metal. In use, these parts are cleansed and sterilized for reuse by conventional means, thereby minimizing the cost of using the injector.

In use, the injector of this invention administers medications and augmentations and, in particularly preferred applications tissue-augmenting amounts of injectable collagen, to laryngeal tissues. such amounts of collagen are from about 0.1 to about 5 ml of collagen suspension.

The collagen which may be used in the injector of the invention may be derived from collagen collected from any number of mammalian sources. Because of their availability, bovine or porcine corium will usually be employed. The preparation of purified substantially nonantigenic collagen in solution from the skin is basically a three-step process involving solubilization, enzyme treatment, and purification. The animal skin is first softened by soaking it in a mild acid and then scraping it to remove hair, epidermis, and fat. The depilated skin is then soaked again in mild acid and then comminuted by grinding, mincing, milling, or like physical treatment. The comminution prepares the skin for solubilization.

The divided tissue may be solubilized under nondenaturing conditions by dispersing it in an aqueous acid medium and digesting with a proteolytic enzyme other than a collagenase. Dilute acid solutions at low temperatures will normally be used to avoid denaturation. Mineral acids such as HCl or carboxylic acids such as acetic, malonic, or lactic acids may be used at pHs in the range of about 1.5 to 5 and temperatures of about 5° C. to 25° C. A preferred procedure is to disperse the comminuted tissue in HCl to a concentration of 1 to 5 g/l at a pH of about 2 at 20° C. After the tissue is dispersed, the enzyme is added and the mixture is incubated to permit the enzyme to digest the telopeptide and other solubilizable components of the tissue. Enzymes that attack the telopeptide portion are used. Examples of such enzymes are pepsin, trypsin, chymotrypsin, and papain. Pepsin is preferred because it is active in acid, and is easily deactivated and removed from the solubilized collagen. The enzyme concentration will usually be in the range of about 0.1% to 10% by weight based on the collagen. The incubation period will typically vary from about two days to two weeks. The progress of the solubilization may be monitored by determining the viscosity of the solution. Once the viscosity reaches a substantially constant level, the solubilization is complete. At this point, the enzyme is deactivated (denatured) and removed.

The enzyme may be deactivated by raising the pH of the solution to at least about 7 by adding an alkaline material such as sodium hydroxide. After the enxzyme has been denatured, the solution is treated to remove denatured enzyme and the portions of the tissue that were digested during the solubilization. Various dialysis, sedimentation, and filtration techniques may be used to effect such removal. See U.S. Pat. Nos. 3,949,073, col. 3, lines 10–22, and 4,140,537, col. 5 line 48, to col. 6, line 34. A preferred procedure is to first lower the pH by adding acid and then to clarify the solution by diatomaceous earth sedimentation. the sediment is filtered and the filtrate is concentrated. The concentrate is then fractionated by ion exchange chromatography and further concentrated to produce a substantially pure collagen solution. The amount of collagen in this solution will usually be about 1 to about 20 mg/ml, more usually about 2 to 4 mg/ml. The pH of the solution will be below about 4, usually in the range of 2 to 3.

The collagen is then reconstituted (reaggregated into fibrils) from the solution. The reconstitution is preferably done by neutralizing the solution at reduced temperatures, preferably about 10° C. to 25° C. The ionic strength of the neutralized solution is preferably hypotonic relative to physiological conditions. Ionic strengths in the range of about 0.03 to about 0.1, preferably about 0.06, will typically be used. The neutralization involves raising the pH of the solution by adding an appropriate base or buffer, such as $Na_2HPO_4$ or NaOH, to a level at which the collagen in solution reaggregates into fibrils. Fiber formation occurs under these conditions at pHs in the range of about 4.9 and about 10.0. The final pH is preferably in the range of 5 to 8.

If desired, the fibrous collagen suspension may be cross-linked in a controlled manner to produce a viscous, covalently cross-linked collagen that may be formulated as an injection. Commonly owned European Patent Application No. 83301135.6 describes such injectable forms of cross-linked collagen and the procedures that may be used to make them.

Forms of collagen other than the enzyme-treated bovine collagen described above that meet the requirements of being substantially nonantigenic and injectable may also be used with the injector of the invention. In addition, low viscosity suspensions, solutions or dispersions of other natural or synthetic biopolymers such as proteoglycan can be administered by the injector of this invention. In general, a fluid is considered to have a suitably low viscosity when its viscosity is 3000 cp or lower at 22°, as measured by an oscillating disk viscometer which measures dynamic rather than steady-flow viscosity. A suitable machine for carrying out this measurement is a Nametre Co. Model 7.006 PBD.

What is claimed is:

1. An injector for laryngeal tissue augmentation comprising a fine-gauge hypodermic needle having a hub removably engaging the distal end of a rigid hollow elongate double open-ended connector tube, said elongate connector tube being bent of a length and shape effective to reach from its proximal end in the patient's mouth to its distal end at the laryngeal tissue of the patient, the proximal end of said tube being adapted to removably engage the tips of a plurality of serially inserted hypodermic syringes to effect liquid-tight temporary communication between the contents of the syringe and the lumen of the connector tube, said proximal end of the connector tube being affixed to a receiver which is adapted to removably receive, support, and align each of the syringes in engagement with the proximal end of the connector tube, said receiver having depending therefrom an external handle positioned adjacent to the plunger of a syringe in the receiver to permit one-handed placement and insertion of the needle into the laryngeal tissues and subsequent manipulation of the plunger of said syringe.

2. The injector of claim 1 wherein said elongate connector tube is 200 to 300 mm in length.

3. The injector of claim 2 wherein the needle hub threadably engages the distal end of the connector tube.

4. The injector of claim 3 wherein the syringe and the needle are presterilized and disposable.

5. A system for augmenting laryngeal tissues comprising a laryngeal injector made up of a fine-gauge hypodermic needle having a hub removably engaging the distal end of a rigid hollow elongate double open-ended connector tube, said elongate connector tube being bent and of a length and shape effective to reach from its proximal end in the patient's mouth to its distal end at the laryngeal tissue of the patient, the proximal end of said tube removably engaging the tip of one of a plurality of serially-inserted hypodermic syringes containing collagen laryngeal augmentation material to effect liquid-tight temporary communication between the collagen material in the syringe and the lumen of the connector tube, said proximal end of the connector tube being affixed to a receiver which is adapted to removably receive, support, and align each of the syringes in engagement with the proximal end of the connector tube, said receiver having depending therefrom an external handle positioned adjacent to the plunger of a syringe in the receiver to permit one-handed placement and insertion of the needle into the laryngeal tissues and subsequent manipulation of the plunger of said syringe.

* * * * *